United States Patent [19]

Warga, III

[11] Patent Number: 5,249,912
[45] Date of Patent: Oct. 5, 1993

[54] INSPECTION APPARATUS

[75] Inventor: Philip R. Warga, III, North Canton, Ohio

[73] Assignee: Rohrer Incorporated, Broadman, Ohio

[21] Appl. No.: 984,945

[22] Filed: Dec. 4, 1992

[51] Int. Cl.$^5$ .............................................. B65H 51/00
[52] U.S. Cl. .............................. 414/746.3; 414/746.7
[58] Field of Search ............... 414/431, 746.7, 746.3; 198/411, 412, 836.1, 836.3

[56] References Cited

U.S. PATENT DOCUMENTS

| | | | |
|---|---|---|---|
| 3,064,826 | 11/1962 | Ettinger | 414/746.3 X |
| 3,224,254 | 12/1965 | Loving | 414/431 X |
| 3,705,655 | 12/1972 | Fahrenholz | 414/431 |
| 3,797,686 | 3/1974 | Jarvis | 414/431 |

Primary Examiner—D. Glenn Dayoan
Attorney, Agent, or Firm—Fay, Sharpe, Beall, Fagan, Minnich & McKee

[57] ABSTRACT

An automatic inspection apparatus simultaneously rotates and longitudinally translates cylindrical workpieces through an inspection station. The inspection apparatus includes an infeed station where the cylindrical workpieces are first abutting pre-staged in coaxial alignment between a moving continuous belt and an overhead V-block guide surface. At the inspection station, a second V-block guide surface includes an integral flux transducer for inspecting the workpieces as they longitudinally translate along a linear path in a spaced-apart coaxial relationship. Also, at the inspection station, a second continuous belt is provided moving in a direction angularly related to the linear path for imparting motion to each workpiece causing them to simultaneously rotate about their longitudinal axis and separate from each other and translate along the linear path. Suitable control apparatus and a pneumatic ejector are provided downstream of the inspection station for rejecting bad workpieces.

13 Claims, 6 Drawing Sheets

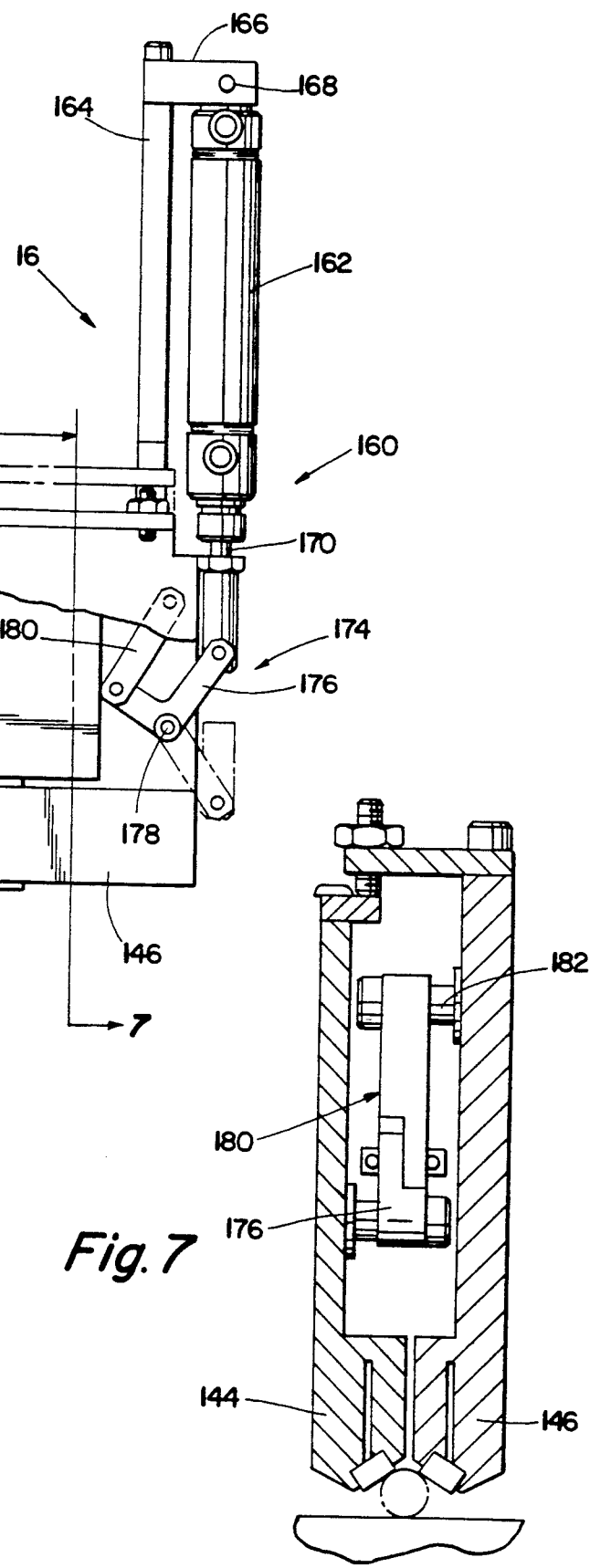

5,249,912

INSPECTION APPARATUS

BACKGROUND OF THE INVENTION

The subject invention is directed toward the art of workpiece inspection and, more particularly, to an apparatus for rotating a cylindrical workpiece about its longitudinal axis and moving it past an inspection station.

The invention is especially suited for use in checking for surface imperfections on cylindrical workpieces and will be described with particular reference thereto; however, as will become apparent, the invention could be used in a variety of situations wherein it is desirable to rotate a cylindrical workpiece about its longitudinal axis and move it in an axial direction past an inspection station.

When inspecting the surface of cylindrical workpieces for flaws and imperfections, it is necessary to perform a series of measurements or checks at both axially and circumferentially spaced points to be certain that the workpiece is within tolerance throughout its length and/or that it meets the necessary requirements. The transfer equipment for presenting the workpiece to the inspection or measuring equipment in a suitable sequence of positions can become somewhat complex. Ideally, the transfer equipment should be capable of being adjusted so that the number, spacing, or width of inspection points or paths can be readily varied.

BRIEF STATEMENT OF THE INVENTION

The subject invention provides a relatively simple apparatus which can move the workpieces in a desirable manner and which can be easily and quickly adjusted to varyinq the presentation of the workpieces at the inspection station.

In accordance with an aspect of the invention, there is provided an inspection apparatus for inspecting cylindrical workpieces. The apparatus generally comprises a work inspection station with a conveying means for conveying the cylindrical workpieces therepast. The apparatus includes a work support carrying a first, upwardly facing planar support surface for supporting the cylindrical workpieces. V-block means are mounted above the work support with adjacent, downwardly facing guide surfaces angularly related to each other and the planar support surfaces. The guide surfaces and the planar support surface are spaced to engage the cylindrical workpieces axially along their exterior cylindrical surfaces and to define a linear path. An endless belt is positioned below the V-block means and has a flat upper run which defines the first, upwardly facing planar support surface. Additionally, power and guide means are provided for driving the endless belt to cause the upper run to move in a direction angularly related to the linear path to thereby impart motion to the workpieces to cause them to rotate about their longitudinal axis and translate along the linear path.

Preferably, and in accordance with a more limited aspect of the invention, the power and guide means include adjusting means for varying the angle at which the upper run of the endless belt moves relative to the linear path. Further, it is preferred that there be means for varying the speed at which the upper run of the endless belt moves.

In accordance with a still further aspect of the invention, it is preferred that the V-block means include means for varying the spacing between the guide surfaces and the planar support surface so that cylindrical workpieces of widely ranged sizes may be inspected.

In accordance with yet another aspect of the invention, the apparatus preferably includes supply means which comprises a pair of opposed, spaced guide members for engaging on diametrically opposite sides of the cylindrical workpieces and aligning them with the linear path while maintaining them in such alignment during movement across the endless belt.

As can be seen from the foregoing, a primary object of the invention is the provision of a simplified apparatus for rotating and translating cylindrical workpieces past an inspection station.

Yet another object of the invention is the provision of an apparatus of the type described wherein the workpieces are moved along a linear path while being simultaneously rotated so that points on their outer surface describe a helical path.

Yet another object of the invention is the provision of an apparatus of the general type described which is particularly suited for checking the diameter of cylindrical workpieces by rotating them about their longitudinal axis while translating them past an inspection station.

BRIEF DESCRIPTION OF THE DRAWINGS

The above and other objects and advantages will become apparent from the following description when read in conjunction with the accompanying drawings wherein:

FIG. 6 is a partial elevational view taken on line 6—6 of FIG. 5 with portions broken away to show the interior of the V-block assembly used at the ejection station; and, FIG. 7 is a cross-sectional view taken on line 7—7 of FIG. 6.

DETAILED DESCRIPTION OF THE PREFERRED EMBODIMENT

Figure 1:
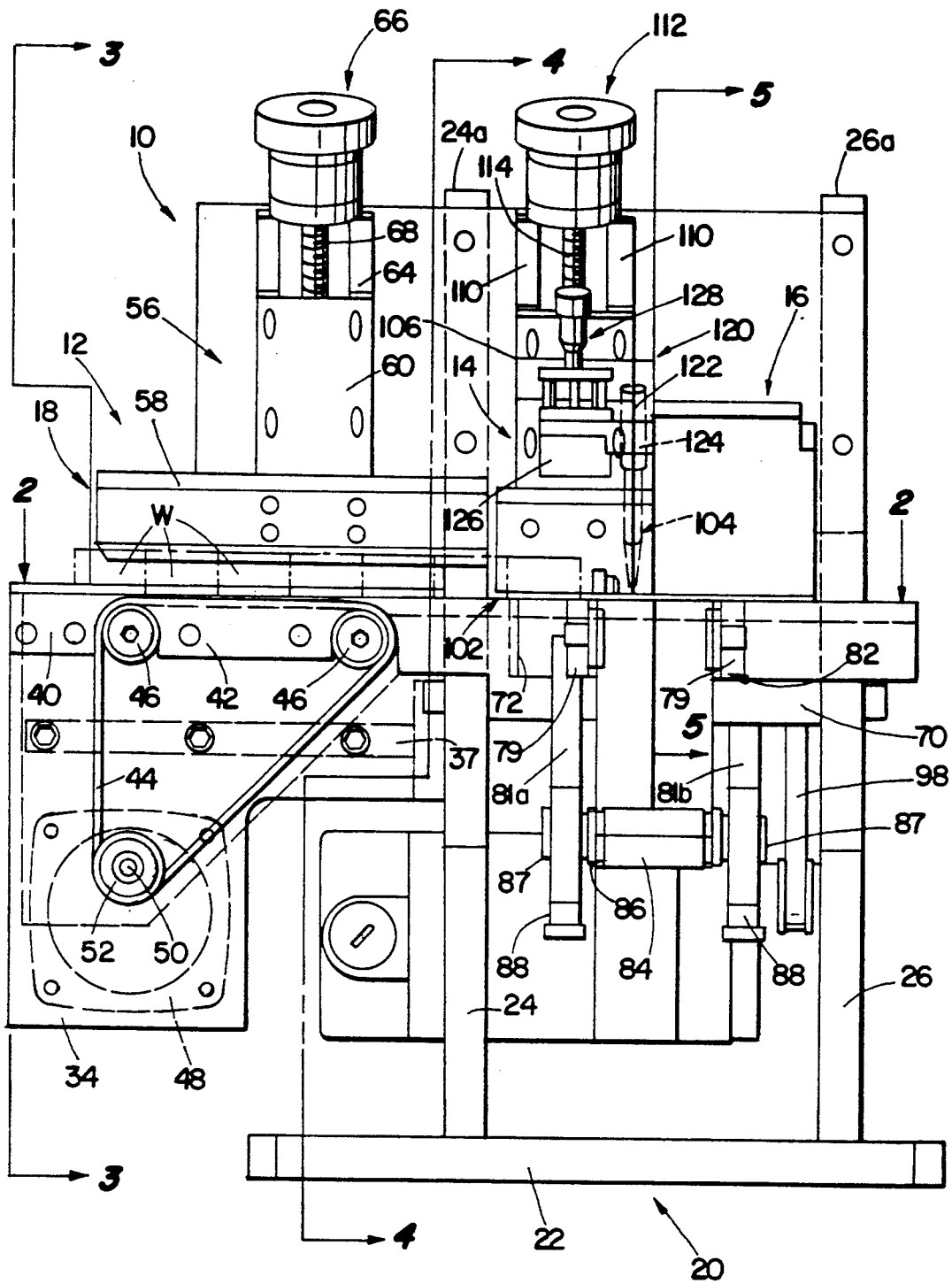
FIG. 1 is a front elevational view of an inspection apparatus incorporating the subject invention.

Referring more particularly to the drawings wherein the showings are for the purpose of illustrating a preferred embodiment of the invention only and not for the purpose of limiting same, FIG. 1 shows the overall arrangement of an inspection apparatus formed to incorporate various aspects of the subject invention. Generally, as shown in FIG. 1, the apparatus 10 includes an infeed station or section 12 which is associated with, and feeds cylindrical workpieces W directly to, a workpiece rotation and inspection station 14. Downstream of the inspection station 14 in the direction of workpiece flow is a reject and discharge station assembly 16.

Broadly, the apparatus is arranged so that the workpieces W are supplied to the inlet end 18 of a linear path which extends transversely across the machine with the workpieces in axial and horizontal alignment. The aligned workpieces are moved axially through the inspection station 14 where they are given a rotary motion about their longitudinal axis so that, in effect, inspection points on each workpiece surface follow a helical path while they pass through the inspection station. The inspection apparatus can be many different types to check various aspects of the cylindrical workpiece including diameter, surface finish and the like. From the inspection station 14, the workpieces W pass through a reject station and discharge assembly 16 wherein those pieces which do not meet the tolerances established are ejected into a discharge or eject chute, as the remaining workpieces which have passed the inspection are directed out the discharge for packaging, further processing or the like.

Figure 2:
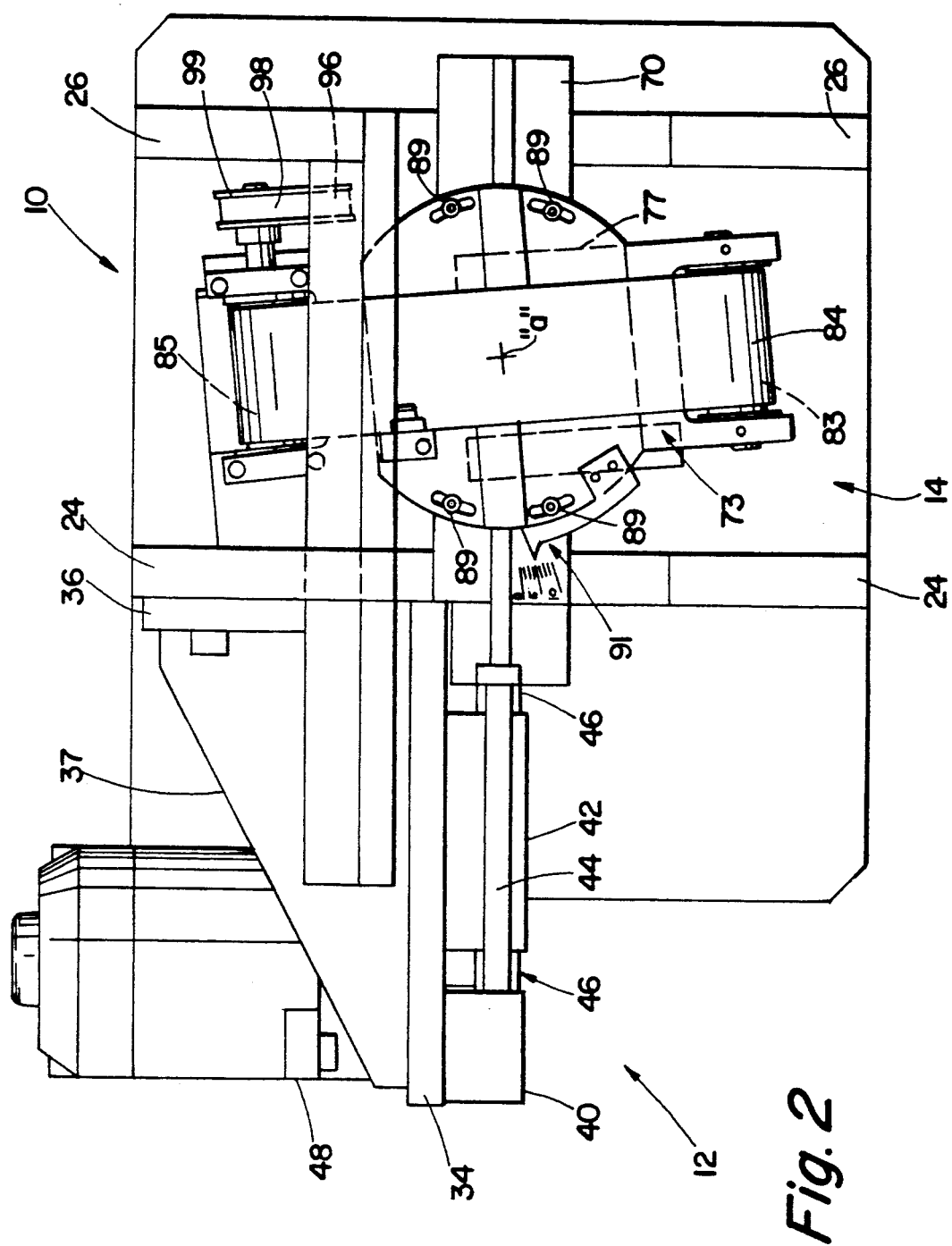
FIG. 2 is a cross-sectional view of the apparatus shown in FIG. 1 (the view is taken on line 2—2)
Figure 3:
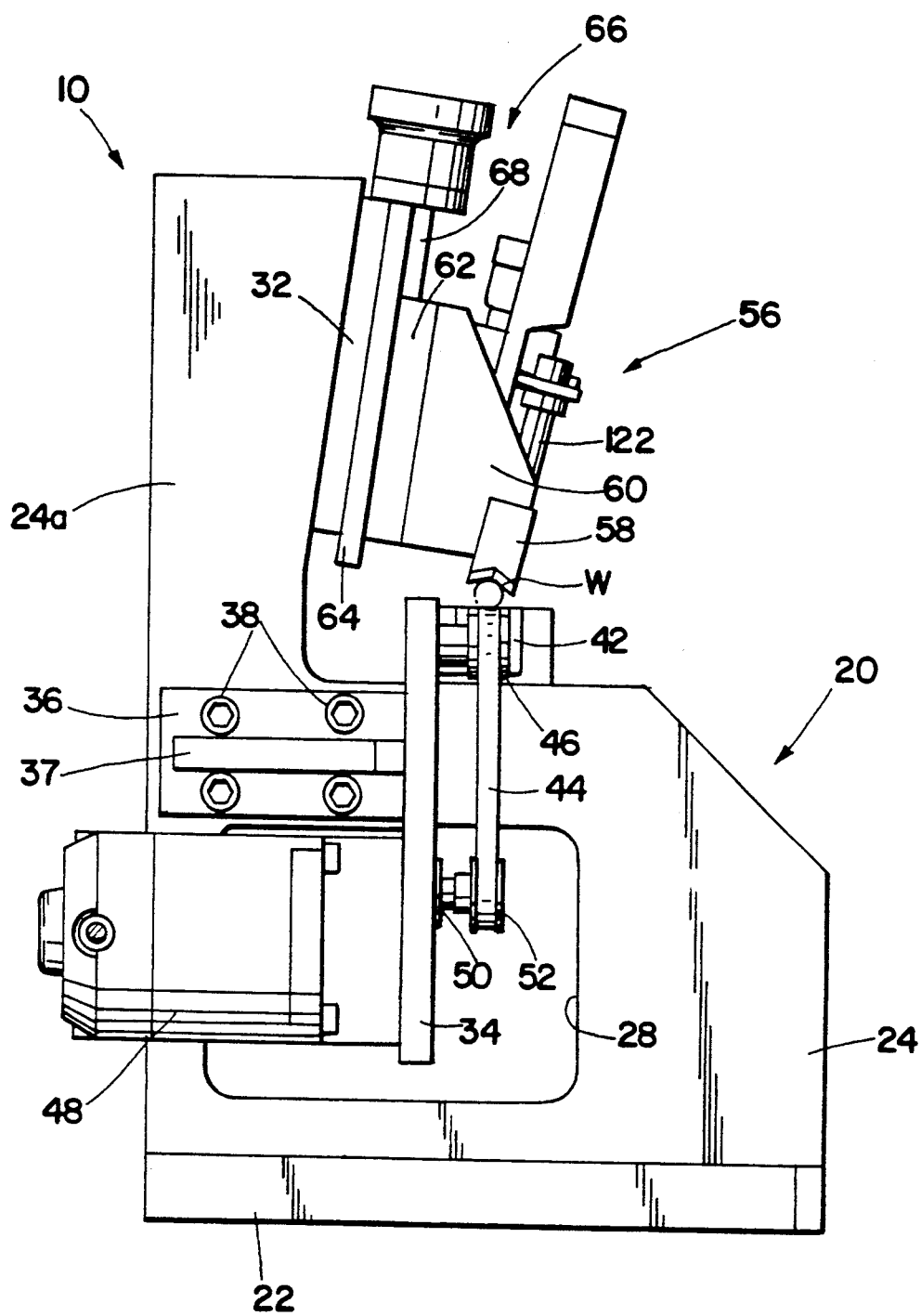
FIG. 3 is an end elevational view taken on line 3—3 of FIG. 1.
Figure 4:
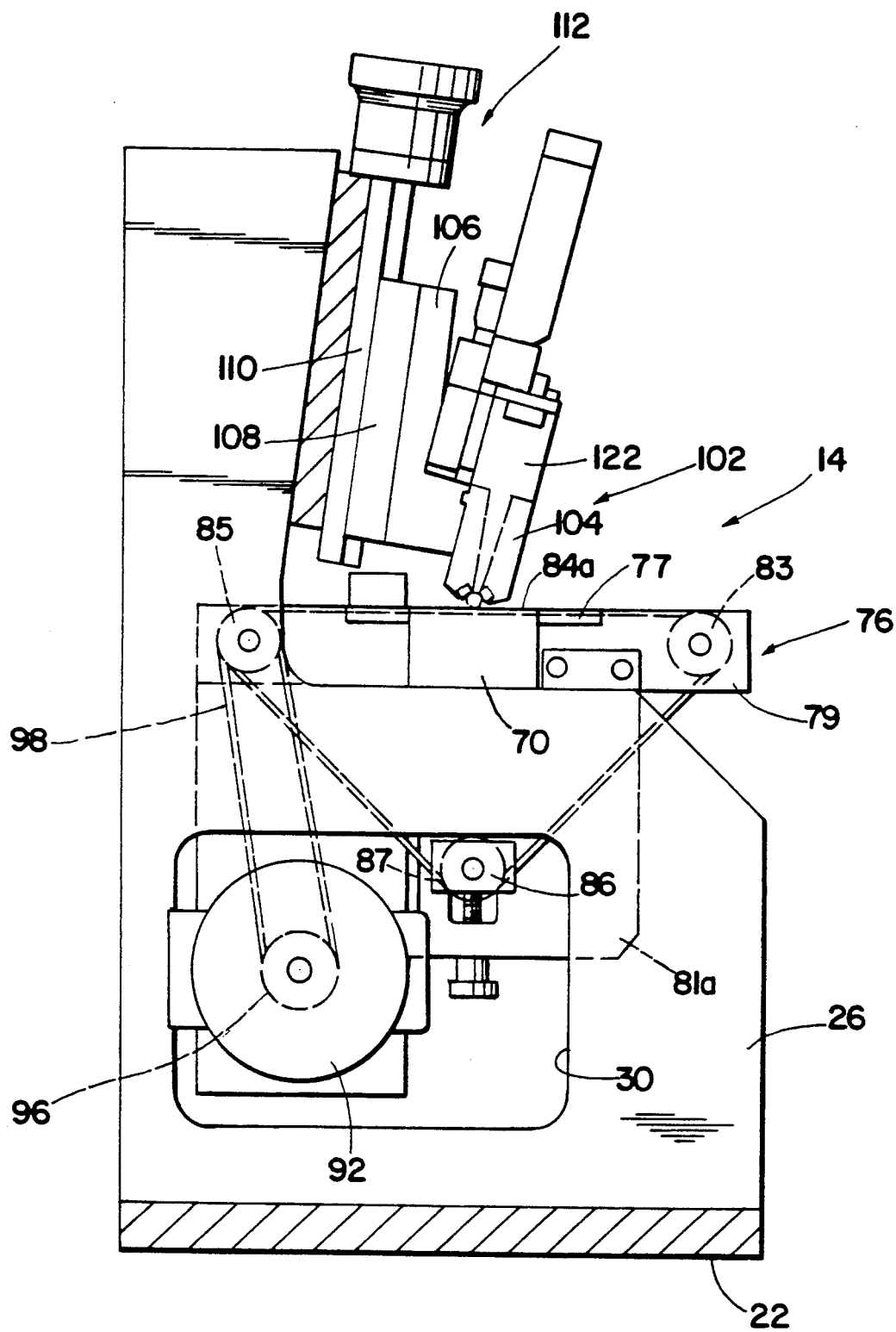
FIG. 4 is a cross-sectional view taken on line 4—4 of FIG. 1.

As best seen in FIGS. 1-3, the overall apparatus includes a main frame assembly 20 which supports the various previously mentioned stations 12, 14, and 16. The frame 20 is illustrated as a relatively rigid assembly formed from steel plate and comprising a main base 22 and a pair of vertically extending, somewhat L-shaped support frame elements 24 and 26. The support frames 24, 26 are suitably bolted or otherwise connected at their lower end to the base plate 22 and extend vertically upward in parallel, side-by-side relationship. The frames have the general shape best shown in FIG. 3. As seen in FIGS. 3 and 4, the plates 24 and 26 each include a rectangular through opening 28, 30, respectively, together with an upwardly extending top section 24a and 26a, respectively. Extending between the upper portions 24a and 26a and connected thereto is a main back support plate 32. Plate 32 is suitably joined to the frame portions 24a and 26a by machine screws or the like, not shown. The back plate 32 supports various portions of the separate stations 12, 14, and 16.

Station 12 is generally carried from a main, vertically extending support plate 34 which is supported from frame plate 24 by a bracket plate 36 and a horizontal plate 37 (see FIG. 3) which extends rearwardly from the plate 34. Bracket plate 36 is joined to the side of frame plate 24 by a plurality of machine screws 38. Joined to the upper edge of the support plate 34 are first and second laterally extending supports 40 and 42 (see FIG. 1) which define upwardly facing support surfaces which form the path along which the workpieces W are translated. As best seen in FIGS. 1 and 2, the support members 40 and 42 are joined to the support plate 34 such as through the use of machine screws or the like. The support member 42 is provided with a central, relatively shallow longitudinally extending groove in its upper surface. Traveling through the groove is an endless flexible belt 44 arranged to be driven in a clockwise direction as viewed in FIG. 1. Preferably, the belt is of the positive drive type. The upper run of the endless belt 44 is constrained and guided by a pair of idler pulleys 46 which are suitably supported with their axis extending horizontally out from the support plate 34.

The belt 44 is selectively driven from an electric drive motor and gear reduction assembly 48 which is mounted from the rear side of plate 34 and has its output shaft 50 extending through plate 34 and carrying a drive pulley 52.

In order to maintain the workpieces W in alignment on the upper run of the endless flexible belt 44, there is provided a V-block type guide assembly 56 which is arranged to engage the upper surface of the workpieces on laterally opposite sides and maintain them in axial alignment on the belt and in engagement therewith. The assembly 56 generally includes an elongated V-block member 58 which has a pair of angularly related V-guide surfaces formed along its lower edge (see FIG. 3). Preferably, the V-guide surfaces are provided with longitudinally extending wear resistant carbide inserts.

The V-block 58 extends horizontally and in alignment with the upper run of belt 44 as can be seen in FIGS. 1 and 3. The block 58 is supported in its center area from a support block 60 that is joined to a guide member 62. Member 62 is constrained in a guide track formed by a pair of side guide elements 64 joined to back plate 32. The assembly is mounted at an angle as shown in FIG. 3 and is arranged so as to be capable of undergoing vertical adjustment through a micrometer type adjusting screw assembly 66. The conventional micrometer type adjusting screw assembly 66 has a downwardly extending screw element 68 that connects to the slide block 62. This arrangement allows the position of the V-block element 58 relative to the belt 44 to be adjusted so as to allow the assembly to handle workpieces of varying diameters.

As noted earlier, the workpieces pass from the input section 12 to the inspection section 14 wherein they are translated along the horizontal path and simultaneously rotated so that they move with a helical rotary motion as they pass the inspection station. As best seen in FIGS. 1, 2, and 4, the inspection station 14 includes a drive belt assembly which is supported from a main horizontally extending support beam 70 which is mounted between the frame side plates 24, 26. The beam 70 has a central U-shaped opening 72 in which is carried an endless belt assembly 73 mounted for adjustable angular orientation in directions transversely of the path of movement of the workpieces.

The angularly oriented belt assembly 73 generally comprises a main frame 76 which includes an upper, horizontally mounted plate 77 having a generally circular configuration as best shown in FIG. 2. The plate 77 carries a pair of downwardly extending, spaced parallel support frame members 79 which, in turn, carry a second pair of spaced support members 81. Suitably pulleys 83 and 85 are mounted at the opposite ends of the first pair of spaced frame members. Pulley 83 is an idler pulley and is suitably mounted in bearings at the forward end of the side frame members 79. Pulley 85 is mounted in parallel relationship thereto and is driven in a manner subsequently to be described. An idler pulley 86 is carried between the second pair of frame members 81 at the lower end thereof and is provided with adjustable bearing blocks 87 mounted for vertical adjusting movement by the adjusting screws 88 illustrated and shown in FIG. 4.

The frame 76 is mounted for rotation about a vertical axis "a" which intersects the horizontal path of movement of the workpieces W. As shown in FIG. 2, the belt assembly 73 can be adjusted and locked in selected positions of adjustment by socket head machine screws 89 which extend through slotted arcuate openings in the plate 77 and are received in threaded openings in beam 70. As can readily be seen by loosening the screws 89, the angular orientation of the frame 76 relative to the path of movement of the workpieces can be readily adjusted. The assembly preferably includes an indicator 91 to designate the angular orientation or the degree of angular orientation relative to the path of movement of the workpieces.

A belt 84 is trained about the pulleys 83, 85, 86 and extends transversely of the path of movement of the workpieces W between pulleys 83 and 85. Its upper run 84a is driven to the right as shown in FIG. 4. The lower run of the belt 84 is trained about the previously mentioned idler pulley 86. Pulley 86 is supported in adjustable bearing blocks 88 which are mounted for vertical adjusting movement in side plate members 81a, 81b that extend downwardly from the upper frame members. The driven pulley 85 (as viewed in FIG. 4) is driven from a motor and gear reducer unit 92. The motor and gear reducer unit 92 is supported from the frame member 81a. The output shaft of the motor and gear reducer unit 92 carries a driven pulley 96 that is connected through a belt 98 to a drive pulley 99 carried on the outer end of the shaft of driven pulley 85.

As previously discussed, the frame assembly carrying the belt 84 is arranged for adjusting positioning about the vertical axis "a". This allows the angle with which the upper run of belt 84a intersects the axis or path of movement of the workpieces to be adjusted. By adjusting this angle and the speed of the belt 84, the speed of rotation and translatory or helical path movement of the workpieces can be adjusted.

The workpieces are maintained in their alignment with the path of movement as they pass across the belt 84 by and overhead V-block assembly 102 (see FIG. 4) which is positioned at an angle with respect to the vertical axis "a" and has a main V-block element 104 which extends into engagement with its V surfaces acting to engage and guide the upper surface of the workpieces as they go therepast. The V-block member 104 is joined to a support block 106 carried from an adjusting guide block 108. The block 108 is suitably guided for movement in side guide tracks or members 110 which are positioned in parallel spaced apart relationship and extend outwardly from the main back frame member 32. An adjusting mechanism in the form of a conventional micrometer adjustment screw assembly 112 is connected to provide fine vertical adjustment of the adjusting guide block 108 through a downwardly extending threaded screw 114. This allows fine adjustment of the V-block 104 to permit adjustment of the spacing of block 104 above belt 84.

As can be seen from FIG. 1, the length of the V-block member 104 is such that it extends approximately completely across the belt 84. As the workpieces W are conveyed under the guide block 104 by the belt 44, they engage the belt 84 and are given a rotary motion. The belt 84 is running at an incline as shown in FIG. 2. This imparts a helical rotation and translatory drive to the workpieces. By controlling the angle of belt 84 and the speed of its movement, it is possible to cause each workpiece, as it engages the belt, to accelerate axially and pull away from the succeeding workpieces and be conveyed to the right across belt 84 as viewed in FIG. 4. During this movement, various testing or inspecting procedures are carried out.

For this purpose, and as shown in FIGS. 1 and 4, the subject invention includes an inspection station 120 which is arranged in direct association with the guide block 104. As illustrated, the inspection station 120 includes a conventional eddy current flaw detector 122 which extends downwardly through a suitable opening in the guide V-block 104 into close proximity with the workpieces passing thereunder and across the belt 84. The eddy current detector 122 is a conventional unit and is mounted for vertical adjustment to allow it to be set to the most desirable location depending upon the type and size of cylindrical workpiece passing thereunder. In the subject embodiment, the adjusting means comprise a first support arm 124 which is carried from a vertically adjustable guide block 126. The guide block 126 is mounted in suitable guideways carried from the guide block 108. The guide block 126 is selectively adjustable in a vertical direction relative to guide block 108 by a conventional micrometer screw adjustment mechanism 128.

As previously mentioned, as the workpieces pass under the V-guide block 104 and transverse across the inclined belt 84, their outer surfaces move in a helical path past the eddy current inspection device. By adjusting the angle of inclination of the belt 84 and the speed of the belt, it is possible to control the path of the workpiece surface which is scanned by the eddy current surface inspection device 122. Those workpieces which are determined by a suitably programmed control apparatus to not be of suitable surface condition are, immediately after passing over the belt, ejected from the apparatus at the rejection and discharge station 16. Station 16 is best seen and understood with reference to FIGS. 5 through 7. Broadly, station 16 comprises a V-block assembly 142 which is in the path of movement of the workpieces and is aligned with the other V-block assemblies 104 and 58. The V-block assembly 140 can best be understood by reference to FIG. 5 which shows that it is mounted in common with the V-block 104 and carried from the guide block 108 for vertical adjustment.

Figure 5:
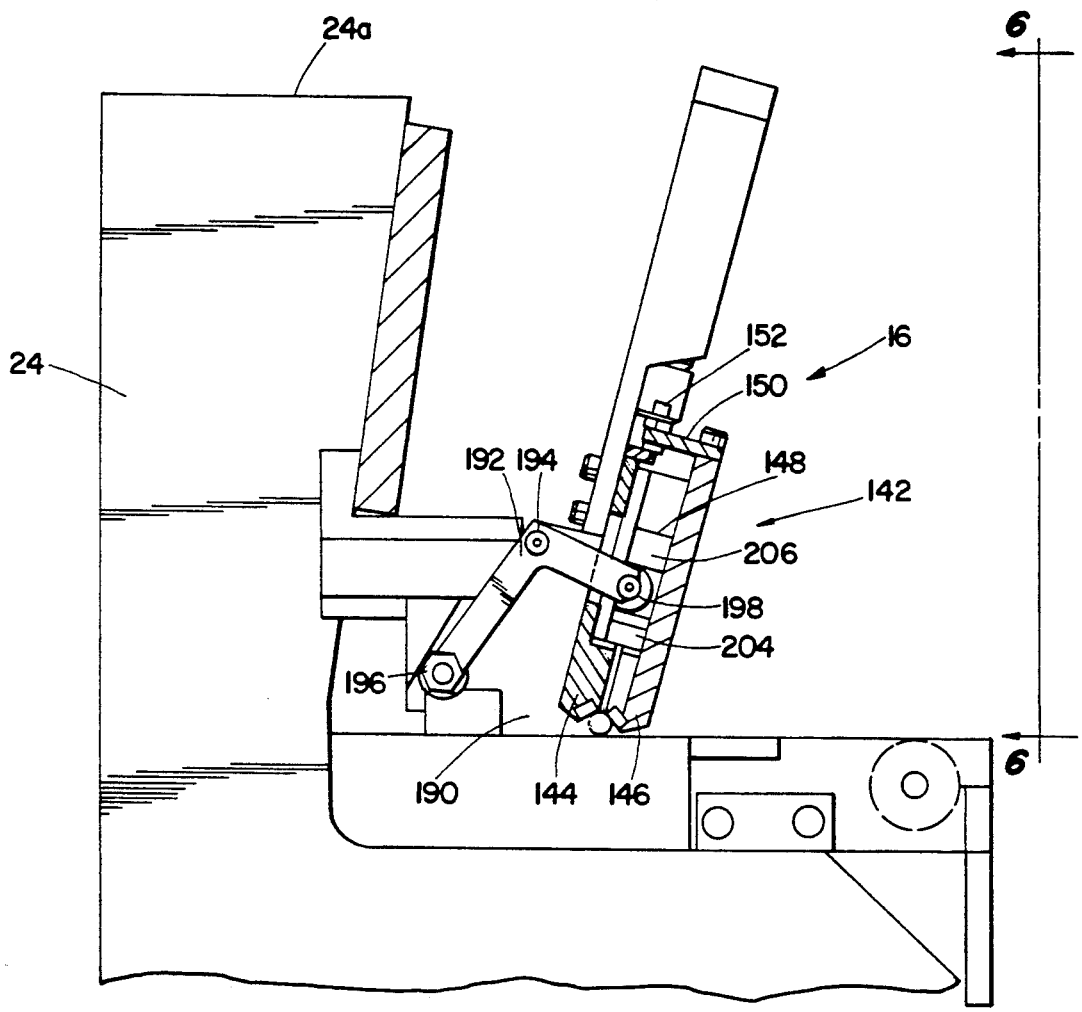
FIG. 5 is a partial cross-sectional view taken on line 5—5 of FIG. 1 and showing the eject mechanism.

As viewed in FIG. 5, the left-hand half 144 of the V-block assembly 142 is directly connected and fixedly secured in aligned position with the corresponding left-hand section of the V-block 104. The right-hand section 146 is, however, designed to undergo vertical reciprocation relative to the left-hand section 144. For this reason, section 146 is suitably connected and supported from section 144 by an internal guide block assembly 148 which permits vertical sliding movement relative to section 144 while maintaining the relative laterally spaced position of the two components. It should be noted that a rearwardly extending bracket plate 150 is connected to the upper ends of section 146 and has stop or adjusting screws 152 to allow precise adjustment and positioning of the lowermost vertical position of section 146.

Selective vertical movement of the section 146 to take it upwardly and allow movement of a workpiece in a direction outwardly to the right from the path of movement through the apparatus (as viewed in FIG. 5) is achieved through the use of an actuating system 160. The actuating system 160 is best seen in FIGS. 6 and 7 and comprises a double-acting air cylinder 162 which is suitably supported from an upwardly extending support arm 164 and a laterally extending bracket 166. The upper end of the air cylinder 162 is pinned to the support arm 166 by a transverse pin 168. The piston rod 170 of the air cylinder 162 is connected through a lever assembly 174 so as to produce a full cycle or vertical upward and return downward movement of the V-block section 146 when the cylinder is actuated to either ends of its stroke. In this regard, the actuating lever assembly 174 includes a first L-shaped crank lever 176 pivotally mounted at its mid-point 178 to the left-hand section (see FIG. 7) 144 of the V-block assembly 140. At its right-hand end, as viewed in FIG. 6, the lever 176 is pivotally connected to the lower end of the piston rod 170. At its left-hand end, the crank 176 is pivotally connected to a connecting link 180 which is, in turn, connected at its upper end to a pin member 182 extending to the left (as viewed in FIG. 7) from the right-hand V-block section 146. As can be appreciated, as the air cylinder 162 is actuated to drive its piston rod 170 downwardly, the crank 176 is moved toward the dotted line position forcing the section 146 of the V-block assembly 140 vertically upward and then back downwardly. During the time the section 146 is moved upwardly, the workpiece which has been found to be defective can be ejected laterally from beneath the V-block assembly.

Simultaneously with the movement of the right-hand V-block section 146 to an upper position, an eject member is moved to engage the defective workpiece and rapidly move it out of the normal path of travel of the remaining workpieces. This mechanism can best be seen in FIG. 5 and includes the eject member 190 which has the general shape shown in FIG. 5 and extends through a suitable slot formed in the sections 144 and 146 of the V-block assembly 140. This arrangement can be seen in FIG. 6. Movement of the eject member 190 to the right (as viewed in FIG. 5) is accomplished through a bell crank lever 192 which is carried from the support mechanism for the eject mechanism 142. This bell crank member 192 is pivoted from the support structure at 194 and has its lower end pivotally connected at 196 to the left-hand or rear portion of the eject member 190 as shown.

The right-hand end of the crank member 192 is provided with a roller member 198 which extends into the center located position shown in FIG. 5. The crank arm itself extends through a suitable window or opening 200 formed at the location best seen in FIG. 6. This allows free oscillating motion of the crank arm 192 to take place and the roller 198 is suitably captured between rearwardly extending guide members 204 and 206 carried on the right-hand V-block section 146. Thus, as can be seen, when the V-block section 146 is actuated upwardly, the bell crank 192 is moved to cause the eject member 190 to move into and through the openings in the V-block sections 144 and 146. This, of course, takes place simultaneously with the upward movement of section 146 and rapidly discharges the defective workpiece in a rightward direction as viewed in FIG. 5.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. Apparatus for conveying cylindrical workpieces past an inspection station comprising:
    a work support carrying a first upwardly facing planar support surface for supporting the cylindrical workpieces;
    V-block means mounted above the work support with adjacent downwardly facing guide surfaces angularly related to each other and the planar support surface, the guide surfaces and the planar support surface being spaced to engage the cylindrical workpieces axially along their exterior cylindrical surfaces and define a linear path;
    an endless belt positioned below the V-block means and having a flat upper run which defines the first upwardly facing planar support surface; and,
    power and guide means for driving the endless belt to cause the upper run to move in a direction angularly related to the linear path to impart motion to the workpieces to cause them to rotate about their longitudinal axis and translate along the linear path.

2. The apparatus as defined in claim 1 wherein the power and guide means include adjusting means for varying the angle at which the upper run moves relative to the linear path.

3. The apparatus as defined in claim 1 including supply means for supplying said cylindrical workpieces to said linear path.

4. The apparatus as defined in claim 1 wherein the power and guide means include means for varying the speed at which the upper run moves.

5. The apparatus as defined in claim 1 wherein said V-block means includes means for varying the spacing between the guide surfaces and the planar support surface.

6. The apparatus as defined in claim 1 wherein each of the guide surfaces are flat and extend parallel to the support surface.

7. The apparatus as defined in claim 1 wherein the guide surfaces are formed to have a significantly lower co-efficient of friction than the upper run of the endless belt.

8. The apparatus as defined in claim 1 including supply means for feeding cylindrical workpieces to the linear path.

9. The apparatus as defined in claim 8 wherein the supply means comprises a pair of opposed spaced guide members for engaging on diametrically opposite sides of the cylindrical workpieces and aligning them with the linear path.

10. The apparatus as defined in claim 9 including means for adjusting the spacing between said guide members.

11. The apparatus as defined in claim 10 wherein said supply means further includes a powered conveyor belt located beneath said guide members and aligned with the linear path.

12. The apparatus as defined in claim 1 wherein the guide surfaces extend laterally beyond the width of the upper run of the endless belt.

13. The apparatus as defined in claim 12 including means for varying the spacing between the guide surfaces and the planar support surface.

* * * * *